(12) United States Patent
Nelin et al.

(10) Patent No.: US 7,264,603 B2
(45) Date of Patent: Sep. 4, 2007

(54) ORTHOPEDIC ARM SLING

(76) Inventors: Karen L. Nelin, 171 Christian Ave., Stony Brook, NY (US) 11790; Marianne Pollaci, 41 Middle Island Ave., Medford, NY (US) 11763

( * ) Notice: Subject to any disclaimer, the term of this patent is extended or adjusted under 35 U.S.C. 154(b) by 6 days.

(21) Appl. No.: 11/221,829

(22) Filed: Sep. 9, 2005

(65) Prior Publication Data

US 2006/0189906 A1 Aug. 24, 2006

Related U.S. Application Data

(60) Provisional application No. 60/593,894, filed on Feb. 22, 2005.

(51) Int. Cl.
*A61F 13/00* (2006.01)
(52) U.S. Cl. .......................................................... 602/4
(58) Field of Classification Search .................. 602/4, 602/20, 5; 2/44, 45; 128/869, 877, 878, 128/879, DIG. 15; D24/190
See application file for complete search history.

(56) References Cited

U.S. PATENT DOCUMENTS

| | | | |
|---|---|---|---|
| 4,716,895 A | 1/1988 | Marques et al. | |
| 5,628,721 A * | 5/1997 | Arnold et al. | ................. 602/19 |
| 5,772,617 A | 6/1998 | Lay | |
| 6,030,354 A * | 2/2000 | Lakusiewicz | .................. 602/4 |
| 2004/0149293 A1 | 8/2004 | Freedman | |

\* cited by examiner

*Primary Examiner*—Kim M. Lewis
(74) *Attorney, Agent, or Firm*—Richard C. Litman

(57) ABSTRACT

The orthopedic arm sling is a sling designed to stabilize the shoulder and arm of an infant, toddler and child. The orthopedic arm sling includes a sling trough and a plurality of neck straps that allow the arm of the user to be supported within the trough and suspended from the user's neck. A pair of torso straps secures the trough about the user's torso, limiting abduction of the extremity. A mesh panel is integrally connected to the sling trough to provide for increased ventilation to the user's forearm and hand. A pair of L-shaped and edge strips of hook and loop fastening material are affixed to a first and second side of the sling trough. When the sling is worn, L-shaped and edge strips of hook and loop fastening material are joined together, uniting the first and second sides of the sling trough to further stabilize the extremity.

9 Claims, 3 Drawing Sheets

ORTHOPEDIC ARM SLING

CROSS-REFERENCE TO RELATED APPLICATION

This application claims the benefit of U.S. Provisional Patent Application Ser. No. 60/593,894, filed Feb. 22, 2005.

BACKGROUND OF THE INVENTION

1. Field of the Invention

The present invention relates to arm slings, and particularly to a stabilizing orthopedic arm sling.

2. Description of the Related Art

When an individual injures their humerus or clavicle, unlike a cast, there is little that can be done to ensure that the individual does not overly move his body so that he causes more damage to the injured body part. This problem is particularly problematic for infants, toddlers and children as they tend to be more active than adults and less aware of the best way to care for their bodies. As such, there is little other than a typical sling that may be done to aid children in stabilizing these upper body parts to prevent against additional injury.

Slings do exist that may be used by children, but they are generally designed merely to support the injured arm of the child. These slings do not provide the requisite stability and security necessary to prevent against excessive movement by the child. Additionally, while slings may be used, the material from which they are generally made tends to be fairly hot and uncomfortable. Especially when a sling is being used solely to stabilize the upper body, the fabric tends to cause the individual's arm to perspire. This lack of comfort, particularly for a child, may cause the child to move more, which may further exacerbate the injured humerus or clavicle.

Accordingly, there is a need for an arm sling that adequately stabilizes an individual's arm and upper shoulder and additionally provides enough ventilation to the forearm and hand to provide the user with as much comfort as possible during use of the sling. Thus, an orthopedic arm sling solving the aforementioned problems is desired.

SUMMARY OF THE INVENTION

The orthopedic arm sling is a sling designed to stabilize the upper shoulder and arm of a child. The orthopedic arm sling includes a folded sheet of fabric material defining a sling trough into which an arm is placed and a plurality of straps that allow the arm of the user to be supported within the trough and suspended from the user's neck. A pair of straps fit around the user's torso, limiting abduction of the extremity. A mesh panel is integrally connected to the sling trough in order to provide for increased ventilation to the user's forearm and hand.

A pair of L-shaped strips of hook and loop fastening material are affixed to a first and second side of the sling trough. When the sling is placed about the arm of the user, suspended from the user's neck and fastened about the torso, the L-shaped strips of hook and loop fastening material are joined together, uniting the first and second side of the sling trough. Additional mating strips of hook and loop fastening material are attached along the ends of the first and second side of the trough to aid in stabilizing the first side of the trough against the second side of the trough.

In addition, a pair of mating neck straps are attached to the second side of the sling trough, one at a proximal end of the trough and the other at the distal end of the trough, and are adapted to fasten behind the user's neck. A pair of mating torso straps are connected to the proximal and distal ends of the second side of the sling trough in order to secure the sling about the torso of the user, thereby limiting abduction of the extremity.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
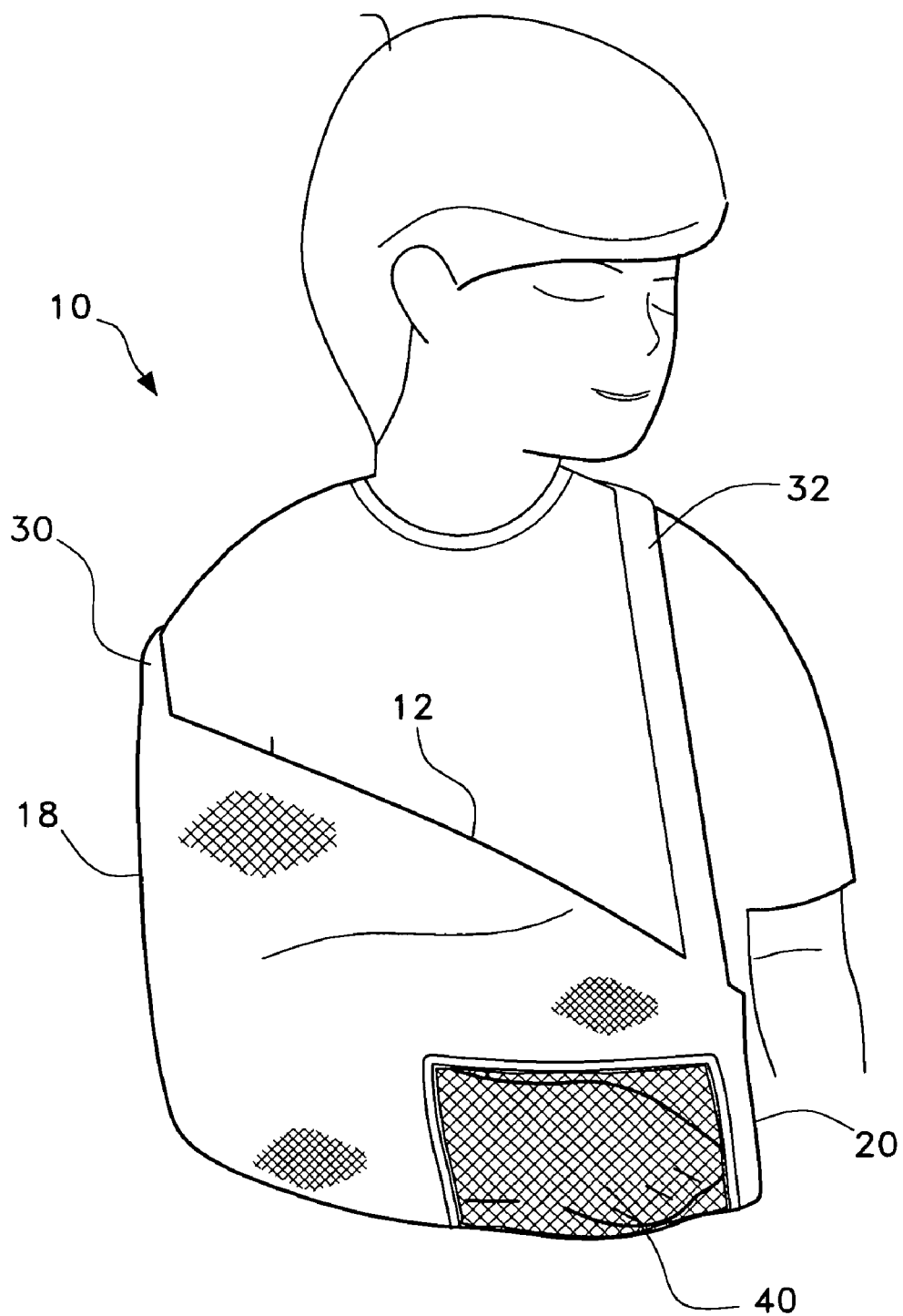
FIG. 1 is an environmental, perspective view of an orthopedic arm sling according to the present invention.

The present invention is an orthopedic arm sling designed to stabilize the upper shoulder and arm of an infant, toddler and child. The orthopedic arm sling, designated generally as 10 in the drawings, is shown supporting a child's arm.

Referring first to FIG. 1, the orthopedic arm sling 10 is shown being used by a child. The arm sling 10 includes a sling trough 12 into which an arm is placed. The elbow of the user nestles into a corner of the sling trough 12 and the arm is supported within the trough 12. A first neck strap 30 is affixed to a proximal end 18 of the trough 12. A mating neck strap 32 is affixed to the distal end 20 of the trough 12. The first neck strap 30 and the mating neck strap 32 attach to one another, as shown more clearly in FIG. 3, with hook and loop fastening strips or any other type of releasable fastener. A mesh panel 40 is integrally connected to the sling trough 12, and medially disposed between the proximal 18 and distal 20 ends of the trough 12. The mesh panel 40 allows for greater ventilation to the forearm and hand.

Figure 2:
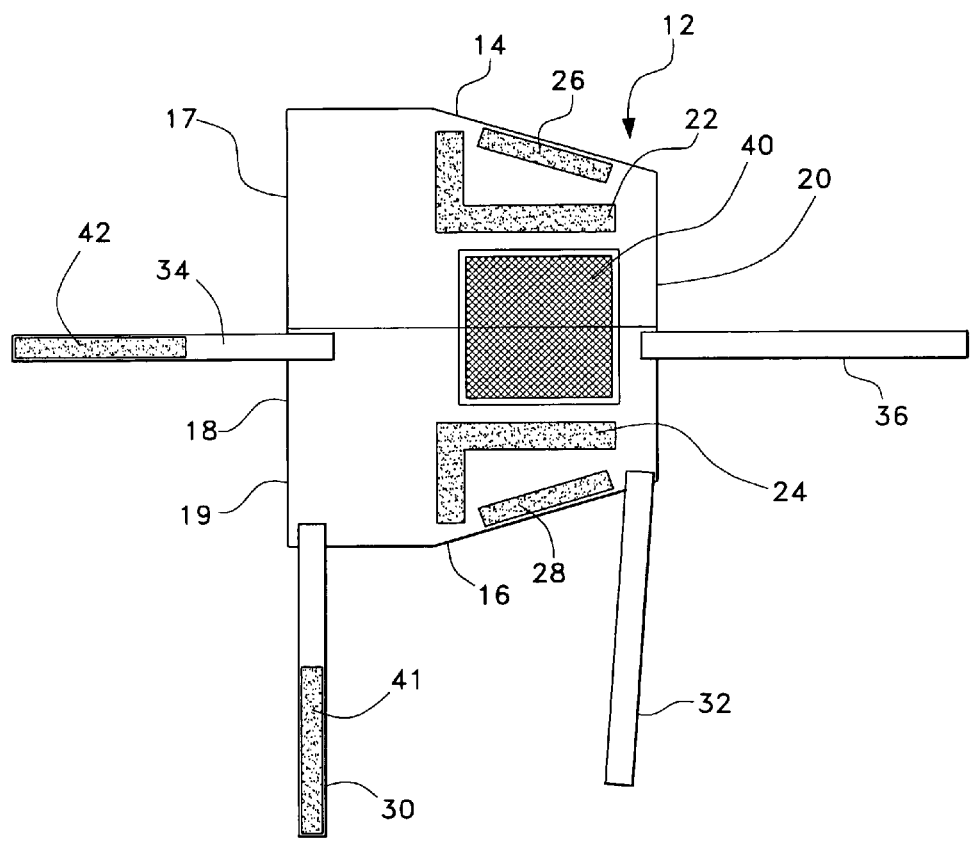
FIG. 2 is a plan view of the orthopedic arm sling according to the present invention.

Referring to FIG. 2, the inward-facing side of the orthopedic arm sling 10 is shown. The orthopedic arm sling 10 includes a folded sheet of flexible material defining a sling trough 12 when the sling 10 is placed about the arm, neck and torso of an individual. The sling trough 12 has a first side 14 and a second side 16, the first side 14 being adapted to fold toward the second side 16 along a crease when the sling 10 is placed about the user's arm, neck and torso. The sling trough 12 has a proximal end 18 (proximal to the shoulder when in use) that is closed so that the elbow of a user is received into the proximal end 18 when the sling 10 is placed about a user's arm, neck and torso. The proximal end 18 has two sections 17 and 19, which are sewn or stitched closed so that the proximal end 18 of the trough 12 forms a pocket into which the elbow of the user is placed. When the sling 10 is placed about the user's arm, neck and torso, the distal end 20 of the sling trough 12 is open, allowing an individual's hand to extend beyond the sling trough 12.

A first L-shaped hook and loop fastening strip 22 is medially attached to the first side 14 of the sling trough 12 between the proximal 18 and distal 20 ends of the trough 12. A mating L-shaped hook and loop fastening strip 24 is medially attached to the second side 16 of the sling trough 12 between the proximal 18 and distal 20 ends of the trough 12. An edge strip of hook and loop fastening material 26 is affixed to the trough 12 along an end portion of the first side 14 of the sling trough 12. A mating edge strip of hook and loop fastening material 28 is affixed to the trough 12 along an end portion of the second side 16 of the sling trough 12.

When the sling trough 12 is worn by a user, the first side 14 of the trough 12 is closed toward the second side 16 of the trough 12. The L-shaped hook and loop fastening strips 22 and 24 are affixed to one another and the edge strips of hook and loop fastening material 26 and 28 are affixed to one another, securing the arm sling 10 about the forearm and upper arm of the user. When worn, the first side 14 of the trough 12 abuts the body of the user, while the second side 16 of the trough 12 faces outward. The first 14 and second 16 sides of the trough 12 are held together by the strips of hook and loop fastening material 22, 24, 26, and 28 attaching to each other.

A mesh panel 40 is integrally attached to the sling trough 12. The mesh panel 40 is medially disposed between the first 14 and second 16 sides of the trough 12 and located between the proximal 18 and distal 20 ends of the trough 12 so that the forearm and hand are able to receive ventilation through the mesh panel 40.

A first neck strap 30 is connected to the proximal end 18 of the second side 16 of the trough 12 and a mating neck strap 32 is connected to the distal end 20 of second side 16 the trough 12. A strip of hook and loop fastening material 41 is affixed to the first neck strap 30. A mating strip of hook and loop fastening material (not shown) is affixed to the underside of the mating neck strap 32 so that when the straps 30 and 32 are wrapped about the user's neck, the straps 30 and 32 are attachable to one another. A first torso strap 34 is medially attached to the proximal end 18 of the trough 12 and the mating torso strap 36 is medially attached to the distal end 20 of the trough 12. A torso strap strip of hook and loop fastening material 42 is affixed to the first torso strap 34. A mating strip of hook and loop fastening material (not shown) is affixed to the underside of the mating torso strap 36 so that when the straps 34 and 36 are wrapped about the user's waist, the straps 34 and 36 are attachable to one another.

Figure 3:
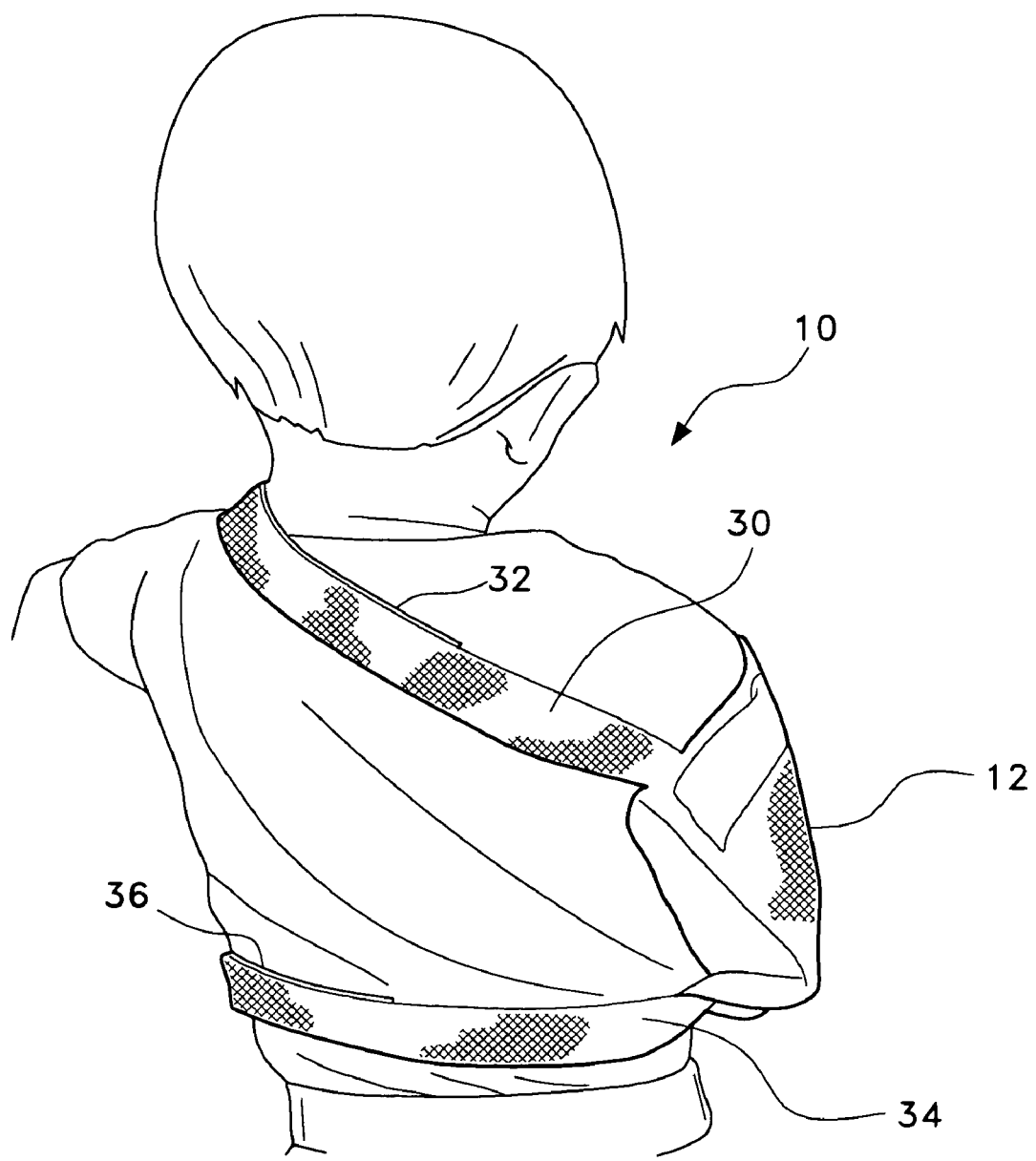
FIG. 3 is an environmental perspective view of the orthopedic arm sling according to the present invention as seen from behind.

FIG. 3 shows a rear environmental view of the orthopedic arm sling 10. The first neck strap 30 and the mating neck strap 32 are fastened to one another. The neck straps 30 and 32 may be attached to one another with hook and loop fastening material or any other type of releasable fastening system that keeps the neck straps 30 and 32 fastened together. When attached, the neck straps 30 and 32 fasten at the nape of the user's neck. The first torso strap 34 and the mating torso strap 36 are adapted to fasten to one another with hook and loop fastening strips or any other type of releasable fastening system that fastens the torso straps 34 and 36 to one another behind the user's back.

While illustrated as being used with a child, the orthopedic arm sling may be used by an adult.

It is to be understood that the present invention is not limited to the embodiment described above, but encompasses any and all embodiments within the scope of the following claims.

We claim:

1. An orthopedic arm sling, comprising: a folded sheet of flexible material defining a perimeter edge and a sling trough for supporting an elbow and a forearm, the sling trough having a first side and a second side, and a proximal end and a distal end; a first releasable L-shaped fastener medially attached to the first side of the trough; a mating second releasable L-shaped fastener medially attached to the second side of the trough; and at least one neck strap connected to the trough and forming a loop adapted to fasten behind a neck of a user; wherein the mating first and second L-shaped fasteners are adapted to fasten the trough closed about the elbow and forearm and does not fasten the perimeter edge when the sling trough is used to support an upper arm, the elbow and the forearm of the user.

2. The orthopedic arm sling according to claim 1, wherein said sling trough further includes at least one mesh panel medially disposed between the proximal and distal ends of the trough.

3. The orthopedic arm sling according to claim 1, wherein the first fastener is a first strip of hook and loop fastening material and the mating second fastener is a second strip of hook and loop fastening material.

4. The orthopedic arm sling according to claim 1, further comprising a first edge fastener attached to an end of the first side of the trough and a mating edge fastener attached to an end of the second side of the trough.

5. The orthopedic arm sling according to claim 4, wherein the first edge fastener and mating edge fastener are strips of hook and loop fastening material.

6. The orthopedic arm sling according to claim 1, wherein said at least one neck strap comprises a first neck strap connected to the proximal end of the second side of the trough and a mating second neck strap connected to the distal end of the second side of the trough, the first neck strap and the mating second neck strap having mating releasable fasteners attached thereto for forming the loop.

7. The orthopedic arm sling according to claim 1, further comprising a torso strap attached to the sling trough.

8. The orthopedic arm sling according to claim 7, wherein said torso strap comprises a first torso strap attached to the proximal end of the second side of the sling trough and a mating second torso strap attached to the distal end of the second side of the sling trough, the first and second torso straps having mating releasable fasteners attached thereto adapted for forming a loop around the user's torso.

9. An orthopedic arm sling, comprising: a folded sheet of flexible material defining a perimeter edge and a sling trough for supporting an elbow and a forearm, the sling trough having a first side and a second side, and a proximal end and a distal end; a first releasable L-shaped fastener medially attached to the first side of the trough; a mating second releasable L-shaped fastener medially attached to the second side of the trough; a torso strap attached to the sling trough, said torso strap comprises a first torso strap medially attached to the proximal end of the trough, and a mating second torso strap medially attached to the distal end of the trough, whereby the sling is secured about the torso of the wearer thereby limiting abduction of the extremity; and at least one neck strap connected to the trough and forming a loop adapted to fasten behind a neck of a user; wherein the mating first and second L-shaped fasteners are adapted to fasten the trough closed about the elbow and forearm and does not fasten the perimeter edge when the sling trough is used to support an upper arm, the elbow and the forearm of the user.

* * * * *